United States Patent [19]

Kiel et al.

[11] Patent Number: 5,464,768
[45] Date of Patent: Nov. 7, 1995

[54] ENHANCED NITRITE PRODUCTION IN TRANSFECTED MURINE CELLS

[75] Inventors: Johnathan L. Kiel; Jill E. Parker; John G. Bruno, all of San Antonio, Tex.

[73] Assignee: The United States of America as represented by the Secretary of the Air Force, Washington, D.C.

[21] Appl. No.: 243,350

[22] Filed: May 16, 1994

Related U.S. Application Data

[63] Continuation of Ser. No. 21,920, Feb. 24, 1993, abandoned.
[51] Int. Cl.⁶ .................................................. C12N 15/85
[52] U.S. Cl. .................... 435/240.2; 435/190; 435/191; 435/240.4
[58] Field of Search .......................... 435/240.2, 240.4, 435/191, 190

[56] References Cited

U.S. PATENT DOCUMENTS

| | | | |
|---|---|---|---|
| 4,839,284 | 6/1984 | Kern et al. | 435/68 |
| 4,997,930 | 3/1991 | Lahners et al. | 537/27 |
| 5,003,050 | 3/1991 | Kiel et al. | 534/573 |
| 5,156,971 | 10/1992 | Kiel et al. | 435/252.31 |

OTHER PUBLICATIONS

Bruno, J. G. et al., (1994) Biochem Biophys. Res. Comm. 201(1), 284–289.

Bruno, J. G. et al., (1992) Fase B. J. 6(5), A1728.

Chong, C. L. et al., (1986) Proc. Natl. Acad. Sec. USA, 1983, 6825–6828.

Miyazaki, J. et al., (1991) Mol. Gen. Genet. 228, 329–334.

Schnorr, K. M. et al., (1991) Mol. Gen. Genet, 227, 411–416.

Primary Examiner—Charles L. Patterson, Jr.
Attorney, Agent, or Firm—Charles E. Bricker; Thomas L. Kundert

[57] ABSTRACT

Mamammalian cell lines capable of enhanced nitrite production are by transfecting a murine macrophage or murine thymoma with barley nitrate reductase gene (NR).

1 Claim, 4 Drawing Sheets

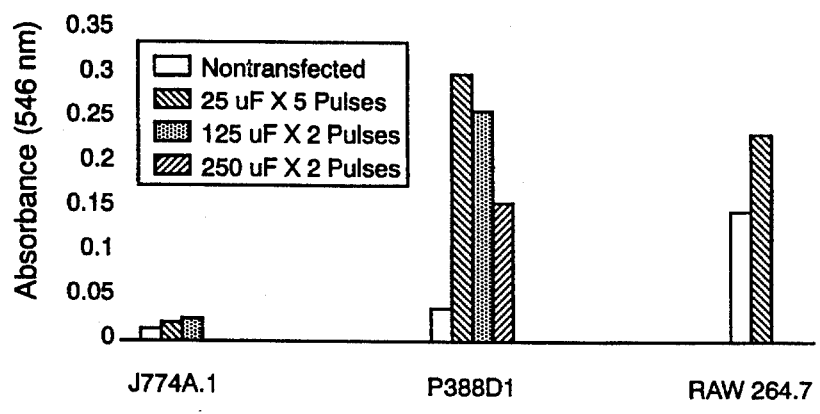
Fig. 1
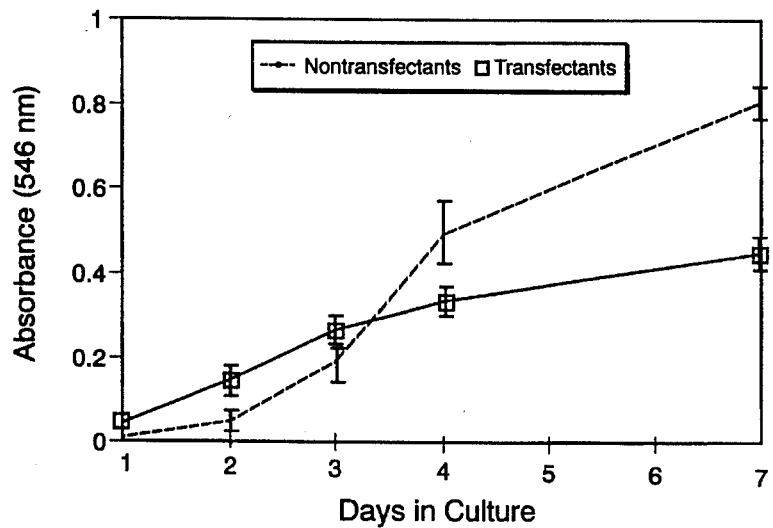
Fig. 2
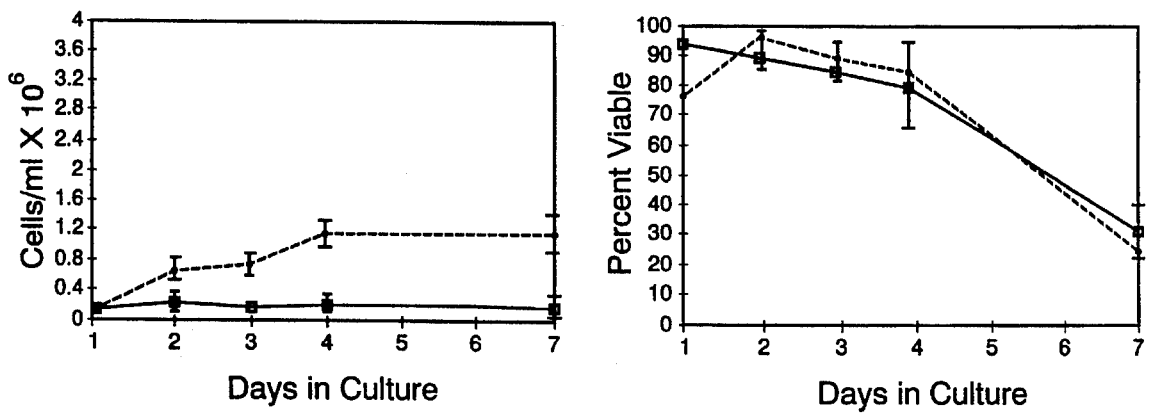
Fig. 3
Fig. 4

ENHANCED NITRITE PRODUCTION IN TRANSFECTED MURINE CELLS

RIGHTS OF THE GOVERNMENT

The invention described herein may be manufactured and used by or for the Government of the United States for all governmental purposes without the payment of any royalty. This is a continuation of application Ser. No. 08/021,920, filed Feb. 24, 1993 now abandoned.

BACKGROUND OF THE INVENTION

This invention relates to the genetic alteration of the metabolism of cells to carry out a desired bioconversion, specifically enhanced nitrite production.

Nitric oxide (NO) has drawn increasing attention for its roles in the vascular, digestive, immune and nervous systems. In these systems NO results, along with its spontaneous oxidation products $NO_2^-$ and $NO_3^-$, from the deimination of L-arginine by an NO synthase (NOS). Two isozymes of NOS have been described in various cell types; a mildly active constitutive NOS (cNOS) and a highly active endotoxin and cytokine inducible NOS (iNOS). Both iNOS and cNOS have been identified in macrophages.

NO has been identified as the endothelial- and neutrophil-derived relaxing factor for vascular smooth muscle cells. Additionally, NO is thought to act as a neurotransmitter or second messenger largely because of its rapid diffusion through cell membranes and ability to increase cGMP levels in affected cells. In the immune system, production of NO, $NO_2^-$ and $NO_3^-$ by phagocyte iNOS requires stimulation from specific ligands such as lipopolysaccharide (LPS) or interretort (IFN). Oxidized nitrogen species are generated by phagocytges as nonoxidative microbicidal, tumoricidal, or inhibitory agents.

The importance of oxidized forms of nitrogen is apparent. Unfortunately, study of NO and $NO_2^-$ is hampered by the short-lived, highly reactive nature of these molecules in biological systems. NO exists as a minor equilibrium product of the breakdown of nitrous acid (the aqueous form of $NO_2^-$) as in the following equation:

$$3\ HNO_2 \rightleftharpoons HNO_3 + 2\ NO + H_2O$$

Hence, development of cell lines which express high levels of these molecules upon induction and in a highly regulatable manner is desirable to further elucidate their roles in cell biology. Also, leukocytes producing high levels of nitrite would be useful as highly regulatable tumor killing agents.

Accordingly, it is an object of the present invention to provide cell lines capable of enhanced nitrite production.

Other objects and advantages of the invention will be apparent to those skilled in the art.

SUMMARY OF THE INVENTION

In accordance with the present invention there is provided a mammalian cell line capable of enhanced nitrite production. This cell line is formed by transfecting a murine macrophage or murine thymoma with a barley plant nitrate reductase (NR) gene fragment.

BRIEF DESCRIPTION OF THE DRAWINGS

In the drawings,

FIG. 1 illustrates nitrite production by 3 macrophage cell lines and the effect of various electroporation protocols on expression of the barley NR gene fragment;

FIG. 2 illustrates mean absorbance values indicating relative nitrite production for transfected (solid line) and nontransfected (dashed line) RAW 264.7 cells cultured in the presence of 39.5 mM $KNO_3$;

FIG. 3 illustrates mean total cell counts for populations depicted in FIG. 2;

FIG. 4 illustrates mean viability data for populations in FIG. 2;

DETAILED DESCRIPTION OF THE INVENTION

Figure 5:
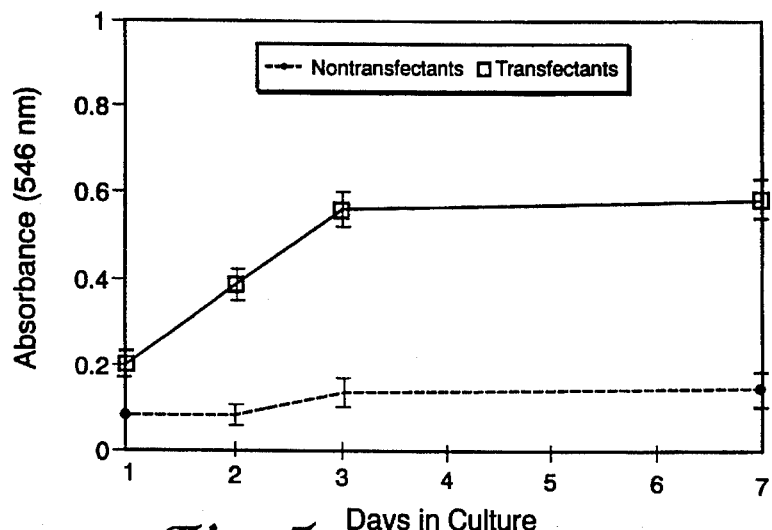
FIG. 5 illustrates mean absorbance values indicating relative nitrite production for transfected (solid line) and nontransfected (dashed line) RAW 264.7 cells cultured in the absence of $KNO_3$.

All cell lines were obtained from the American Type Culture Collection, Rockville, Md. Griess reagents (0.8% sulfanilic acid and 0.5% N,N-dimethyl-alpha-naphthylamine, both in 5N acetic acid) were obtained from Baxter Medical Corp., Sacramento, Calif. $N^g$-monomethyl-L-arginine ($N^g$MMA) and L-canavanine (L-can.) were obtained from Sigma Chem. Co., St. Louis, Mo. and stock solutions of each were prepared in phosphate buffered saline (PBS; pH 7.2). Interferon (INF)-gamma and lipopolysaccharide (LPS) were also obtained from Sigma Chemical Co. Stock solutions of these reagents were made in RPMI-1640 medium without phenol red and without serum and were frozen in small aliquots at −20° C. until used. The Limulus amoebocyte lysate assay kit was also obtained from Sigma. Culture media were randomly tested and did not form gels with amoebocyte lysates (i.e., were negative for LPS contamination).

Plasmid pBcNR/10 containing a 1.1 kb fragment of the barley nitrate reductase gene was obtained from Massachusetts General Hospital, Boston Mass. This plasmid does not contain an antibiotic-resistance gene (used to derive a pure population of transfectants), thus early transfectants made with this plasmid were inhomogeneous and unstable over time. Later experiments involved the use of plasmids constructed by inserting the 1.1 kb and an 800 base pair barley NR gene fragment between EcoR1 sites of the neomycin resistance plasmid pSV2neo. These genetically homogeneous and stable transfected clones were designated $NR10_1$, $NR10_2$ (containing the 1.1 kb piece) and $NR800_5$ (containing the 800 base pair piece). Unless otherwise noted as $NR10_1$, $NR10_2$ or $NR800_5$, data pertain to initial experiments using the unstable transfectants. The bacterium *E. coli*, strain HB101, containing plasmids were grown in M9 minimal medium. The plasmids were amplified with chloramphenicol and extracted by banding twice in cesium chloride gradient. The resulting DNA was extracted with phenol/chloroform and ethanol precipitated. Concentration of DNA was determined spectrophotometrically at 260 nm.

The cells were transfected with the barley nitrate reductase gene by electroporation. Fifty million cells of each cell line were washed twice in cold PBS and suspended in 1 ml of cold RPMI-1640 without serum, phenol red, or antibiotics. Approximately 19 to 30 μg of plasmid DNA containing the barley nitrate reductase gene were added to the cell suspensions which were subsequently left on ice for 10 minutes. Electroporation was accomplished using the Bio-Rad Corp. "GenePulser" apparatus operated at 450V and 25 μFaraday (×5 pulses), 125 μF (×2 pulses), 250 μF (×2 pulses), or 960 μF (×1 pulse) for periods ranging from 0.4 to about 3 μsec depending on the strength of the pulse given.

After pulsing, cells were placed on ice for an additional 10 minutes and transferred to 25 ml of RPMI-1640 with 10% heat inactivated fetal bovine serum (FBS) and allowed to stabilize in culture at 37° C. and 5% $CO_2$ for 3 to 5 days. Cells were gently pelleted to remove dead cells. Stable neomycin-resistant clones ($NR10_1$, $NR10_2$, and $NR800_5$) were routinely passaged in complete RPMI-1640 medium supplemented with 500 μg/ml geneticin (neomycin).

For initial kinetics experiments, cells were transferred by scraping, washed twice in RPMI-1640 without phenol red, and resuspended at $2\times10^5$ cells/ml in RPMI-1640 without phenol red, but, in some cases, with 4 g/l (39.5 mM) $KNO_3$. Cells were then plated in 5 ml aliquots in 6-well tissue culture plates. Cells appeared to tolerate the presence of $NO_3^-$ well and were observed to attach normally in medium containing $KNO_3$. One ml samples of culture supernatants were collected over 7 days for $NO_2^-$ assays. Two hundred μl of each Griess reagent were added per ml of supernatant in polystyrene cuvettes. After mixing, cuvettes were incubated at 37° C., 5% $CO_2$ for 10 minutes and the absorbance of the reaction product was read at 546 nm on a Bausch and Lomb Spectronic 2000 spectrophotometer.

Cells were carefully scraped, briefly treated with 0.5% trypsin at 37° C. and counted using a Coulter Counter model ZM. Viability determinations were performed within 5 minutes of scraping by trypan blue dye exclusion using a hemacytometer. In later experiments, cells were plated at $10^5$ per ml in 0.1 ml aliquots ($10^4$ cells per well) in 96-well tissue culture plates and cultured as before. In these experiments, 0.1 ml of each Griess reagent were added to assay for nitrite and absorbance results were read at 655 nm using a BioRad Model 450 microplate reader. Additionally, cell density was estimated in replicate 96-well plates by staining with Wright-Giemsa stain and reading the absorbance at 405 nm on the microplate reader. Average ratios of the absorbance of the Griess reaction product at 655 nm (nitrite concentration) and the Wright-Giemsa stain at 405 nm (cell density) were used to estimate nitrite production per cell in the presence and absence of exogenous nitrate.

For inhibition studies, to demonstrate cNOS activity, cells were grown to confluence in 6-well plates and washed twice in fresh medium (without phenol red) to remove residual $NO_2^-$. Some wells were treated with media containing various concentrations of $N^gMMA$ or L-can. for 24 hours. Subsequently media were removed and replaced with media containing inhibitors with or without 4 $KNO_2$. $NO_2^-$ assays were performed 24 hours later.

FIG. 1 summarizes the results of $NO_2^-$ assays performed on each macrophage cell line under different electroporation conditions. Nitrite was assayed by spectrophotometric determination of the Griess reaction product at 546 nm. All 3 cell lines were assayed 3 days after electroporation. Data represent values obtained from one determination. Assays for RAW 264.7 cells transfected by the 125 μF×2 pulses and 250 μF×2 pulses protocols were not done. From the figure it is apparent that both transfected and nontransfected J774A.1 cells were less capable of $NO_3^-$ reduction than the other two macrophage lines. The figure suggests that the optimal electroporation protocols were 5 pulses at 25 μF or 2 pulses at 125 μF. Transfection at 960 μF was unsuccessful (data not shown) due to massive cell death at this capacitance. The 25 μF×5 pulses protocol demonstrated the greatest retention of viability (data not shown) and was thus chosen for subsequent experiments.

FIGS. 2–4 illustrate the kinetics of $NO_3^-$ production for RAW 264.7 cells in the presence of 39.5 mM nitrate and correlates these data with data on cell numbers and viability. From FIGS. 2 and 3 it is evident that nontransfected control RAW 264.7 cells produced increasing levels of $NO_2^-$ over time as cell numbers increased. However, transfected RAW 264.7 macrophages demonstrated earlier production of $NO_2^-$ (FIG. 2) and a lack of proliferation over time (FIG. 3). Clearly, $NO_2^-$ production was augmented in transfectants considering their lack of proliferation. FIG. 4 suggests that high $NO_2^-$ levels led to the death of approximately two-thirds of transfected RAW 264.7 cells by day 7. This effect is apparently not related to high cell density stress, as seen in nontransfected cells on day 7, since cell numbers for transfectants remained low throughout the experimental period.

Figure 6:
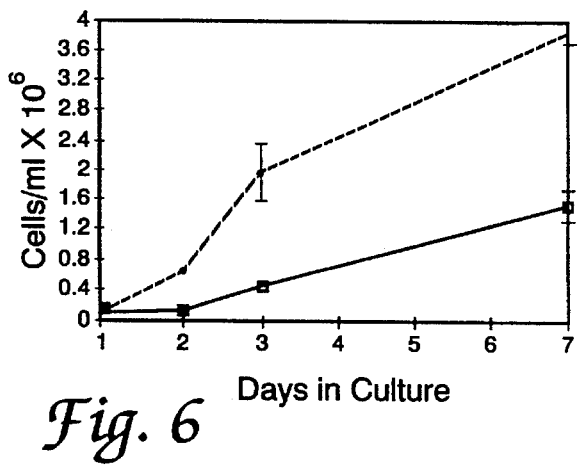
FIG. 6 illustrates mean total cell counts for populations depicted in FIG. 5.
Figure 7:
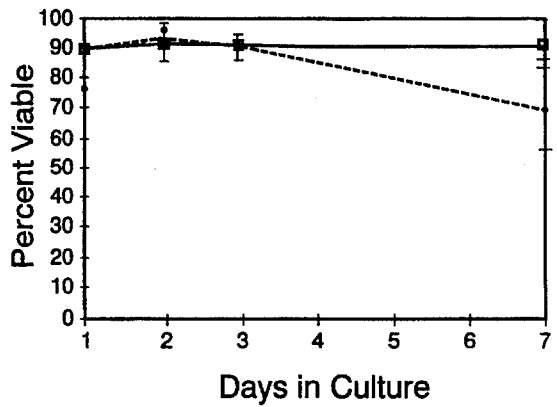
FIG. 7 illustrates mean viability data for populations in FIG. 5.
Figure 8:
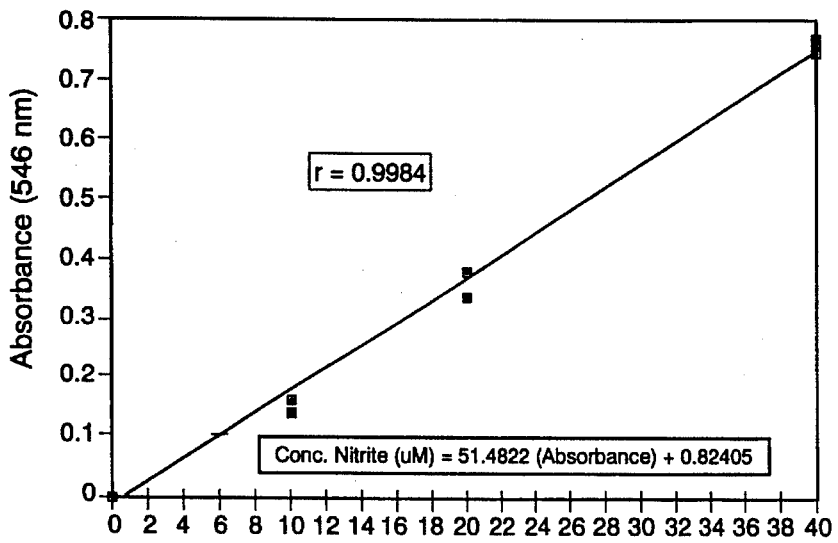
FIG. 8 illustrates a standard curve for nitrite analysis.
Figure 9:
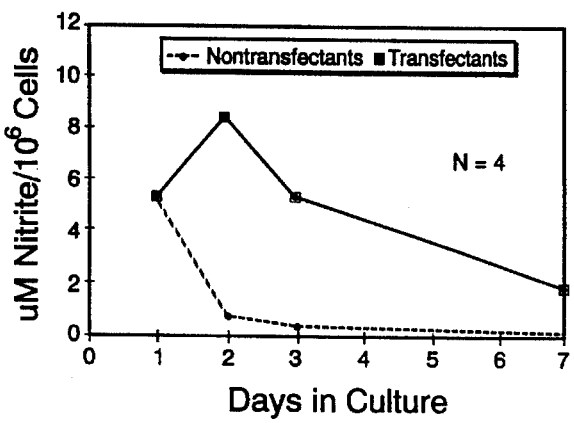
FIG. 9 illustrates comparison of nitrite production per $10^6$ transfected and nontransfected RAW 264.7 cells grown in the absence of nitrate for 7 days. Data represent the mean nitrite concentrations per million cells as determined from data in FIGS. 2–8.
Figure 10:
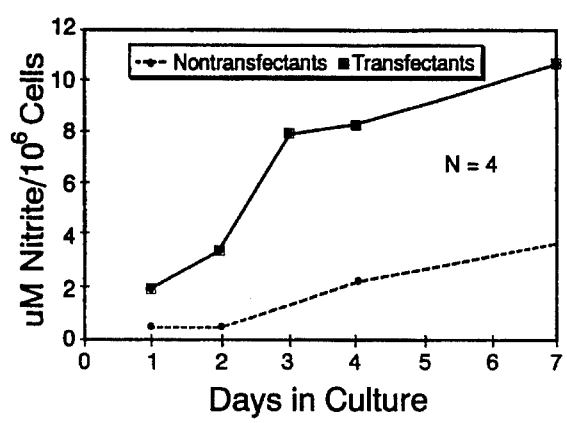
FIG. 10 illustrates comparison of nitrite production per $10^6$ transfected and nontransfected RAW 264.7 cells grown in the presence of nitrate for 7 days. Data represent the mean nitrite concentrations per million cells as determined from data in FIGS. 2–8.

FIGS. 5–7 summarize results of a similar set of experiments conducted in the absence of added nitrate. FIG. 5 illustrates again the enhanced ability of transfectants to produce nitrite. This ability is particularly striking in light of the inhibited proliferation shown by transfectants (FIG. 6). It would appear that low level NOS activity in RAW 264.7 cells supplies nitrate (the ultimate oxidation product of NOS) to a protein coded for by the NR fragment and leads to a self-amplifying loop. Such a mechanism could account for the copious nitrite production seen in FIG. 5, which is difficult to explain in the absence of added nitrate. Viability remained relatively high in both populations (FIG. 7). The curve in FIG. 8 was generated by spectrophotometric assay at 546 nm of serial dilutions of a sodium nitrite solution made in RPMI 1640 without phenol red but with 10% FBS. Data represent raw measurements and the line of best fit from 3 separate determinations. Analysis of standard $NaNO_2$ concentrations as in FIG. 8 enabled calculation of the mean $NO_2^-$ production per $10^6$ cells as seen in FIGS. 9 and 10. It appears that there is a decreasing trend in per capita nitrite production when both cell populations were grown in the absence of added nitrate (FIG. 9). Conversely, there is an increasing trend in both populations when grown in the presence of nitrate (FIG. 10). The slight upward trend among nontransfected controls in FIG. 10 suggests a mild nitrate reductase activity in macrophages which appears to be augmented by transfection with the barley NR fragment.

The nitrite values given in each of the preceding figures should be considered to represent cumulative concentrations, since controls devoid of cells, but containing similar concentrations of $NaNO_2$ demonstrate no loss of $NO_2^-$ after incubation for 10 days (data not shown). The long-term stability of $NO_2^-$ and $NO_3^-$ in culture medium is known. Thus, viability data were not used in calculation of mean $NO_2^-$ concentrations on a per cell basis, since even dead cells may have contributed to the total $NO_2^-$ concentration prior to death.

Figure 11:
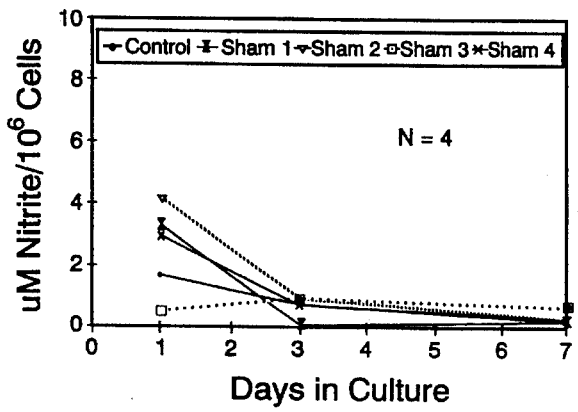
FIGS. 11 and 12 illustrate comparison of nitrite production per $10^6$ sham transfected RAW 264.7 cells, i.e., electroporated but without the NR gene, versus nontransfected control cells in the presence or absence of $KNO_3$.
Figure 12:
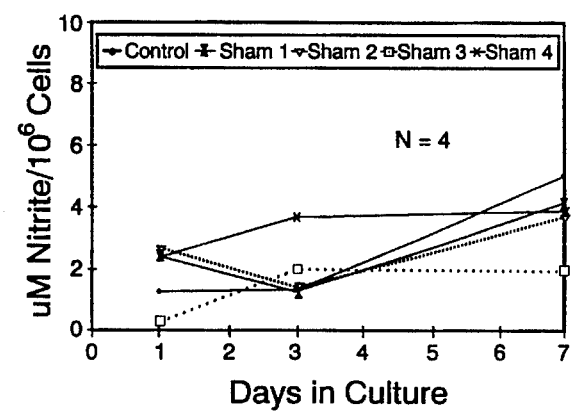

Analysis of "sham" transfected cells (FIGS. 11 and 12) demonstrated that enhanced nitrite production was not due to a nonspecific interaction of macrophages with foreign DNA or the electroporation process. Addition or deletion of various plasmids and the electroporation process from the transfection protocol did not lead to an appreciable divergence from control values. The plasmids chosen were pBr322 and pUC12 (without the NR fragment) in comparable concentrations to those used previously. Sham 1= cells plus pBr322 plasmid. Sham 2= electroporated cells plus pBr322. Sham 3= electroporated cells plus pUC12 plasmid (without the NR fragment). Sham 4= electroporated cells Data on nitrite production per 106 cells for these sham transfections are summarized in FIGS. 11 and 12 and show that little deviation occurred in comparison with the control nitrite levels over 7 days in the presence or absence of added nitrate.

Figure 13:
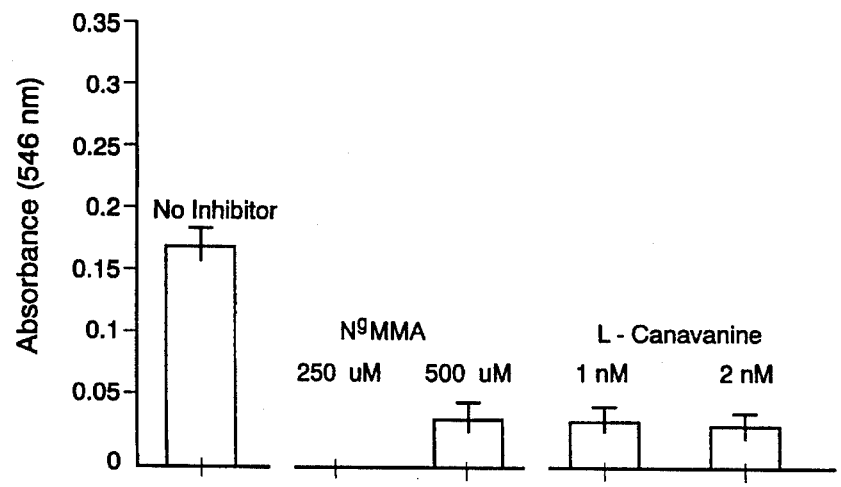
FIG. 13 illustrates the results of cNOS inhibition studies with L-arginine analogs in nontransfected RAW 264.7 cells.

It is somewhat surprising that nontransfected control RAW 264.7 cells produced any detectable nitrite in the absence of stimulation. Culture media have repeatedly shown no evidence of LPS contamination by the Limulus amebocyte assay. Thus, the relatively high nitrite levels in control cultures are not due to endotoxin activation of an inducible NOS (iNOS). A constitutive NOS (cNOS) activity in RAW 264.7 cells may account for the baseline nitrite levels shown here. The baseline generation of $NO_2^-$ by cultures of nontransfected RAW 264.7 cells was demonstrated to be largely inhibited by both $N^g$-monomethyl-L-arginine and L-canavanine (FIG. 13). This observation further suggests that the source of $NO_2^-$ production in control cultures is a constitutive NOS.

Macrophage cell lines clearly exhibit enhancement of nitrite production attributable to transfection with the NR fragment. EL-4 murine thymoma cells also show a slight enhancement of nitrite production following transfection (data not shown). Transfection of the NR gene fragment into other cell lines was not successful, using the procedure described previously. Table I, below, summarizes these data. In the table, a plus (+) indicates that a given cell line showed enhanced nitrite production; a negative (−) indicates that a given cell line did not show enhanced nitrite production. Negative cell lines were transfected and assayed at least twice.

TABLE I

Qualitative Results of Transfection with the Barley Nitrate Reductase Gene Fragment

| Cell Line | Type | Reaction |
|---|---|---|
| RAW 264.7 | Murine Macrophage | + |
| P388D1 | Murine Macrophage | + |
| J774A.1 | Murine Macrophage | + |
| EL-4 | Murine Thymoma | + |
| HL-60 | Human Promyelocyte | − |
| U937 | Human Monoblast | − |
| K562 | Human Erythroblast | − |
| B16 | Murine Melanoma | − |
| HeLa | Human Cervical Carcinoma | − |
| NIH 3T3 | Murine Fibroblast | − |

From the table it can be seen, that transfected leukocytic stem cells such as HL-60, U937, and K562 showed no detectable enhancement of nitrite production. Similarly, transfected cell lines of nonleukocytic origin (i.e., B16 melanoma cells, HcLa, or 3T3 fibroblasts) did not show evidence of augmented nitrite production.

Figure 14:
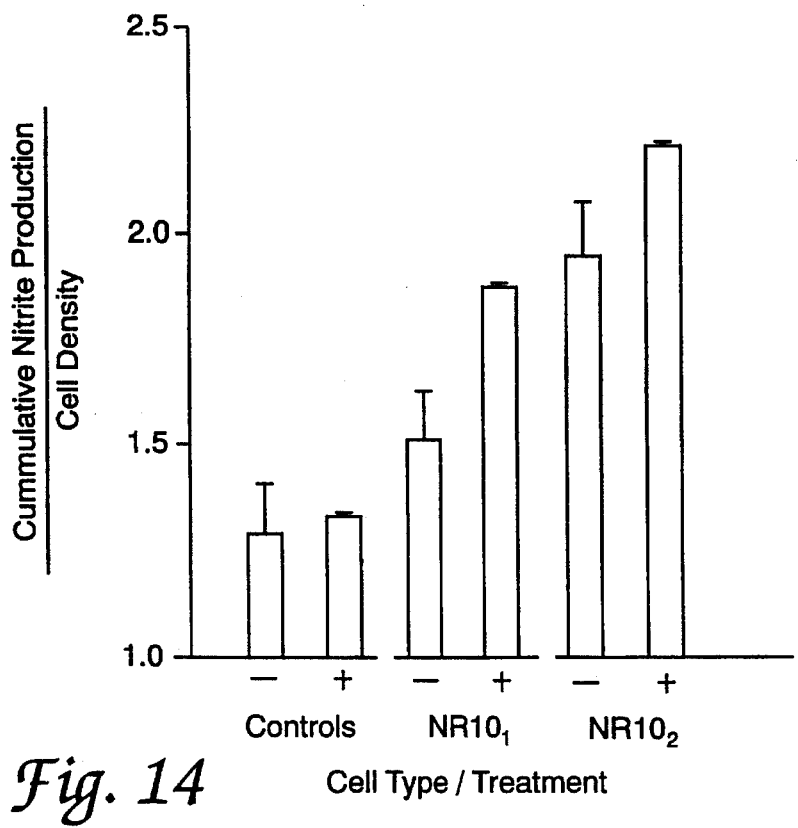
FIG. 14 compares the relative nitrite production per cell of nontransfected control RAW 264.7 murine macrophages with neomycin-resistant clones ($Nr10_1$ and $NR10_2$) on day 1 post-INF-gamma and LPS priming in the presence or absence of added nitrate. Error bars represent ± one SD of the mean (N=16 measurements)
Figure 15:
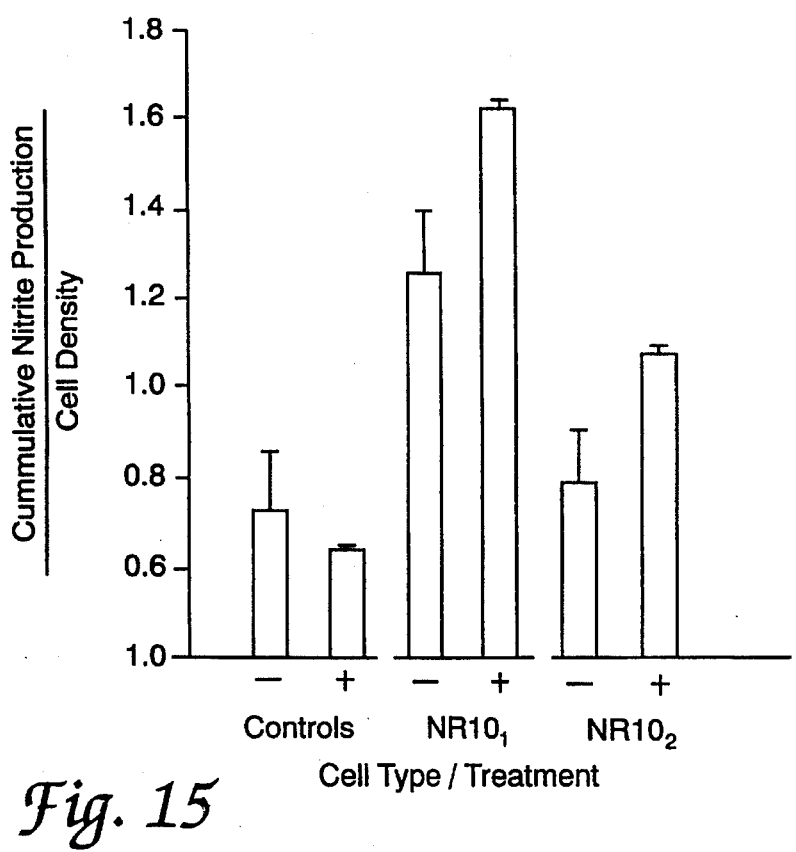
FIG. 15 compares the relative nitrite production per cell of nontransfected control RAW 264.7 murine macrophages with neomycin-resistant clones ($NR10_1$ and $NR10_2$) on day 7 post-INF-gamma and LPS priming in the presence or absence of added nitrate.

Once the neomycin-resistant clones ($NR10_1$, $NR10_2$, and $NR800_5$) had been established by demonstrating that these transfectants survive in the presence of geneticin (neomycin), their nitrate metabolism was studied. Working on the premise that NOS was synergizing with the truncated barley NR protein, experiments in which nontransfected controls and the various new transfectant lines were first primed for 48 hrs. with 5 units/ml of INF-gamma and 10 ng/ml of LPS were conducted. These primed cells were shown to be activated by a rise in their baseline nitrite production. Subsequently, cells were either washed free of INF and LPS or given a second equal dose of the stimulants in the presence or absence of 39.5 mM nitrate. Results of these studies are presented in FIGS. 14 and 15, which illustrate the relative per cell differences in nitrite production between nontranfected control cell populations as well as the $NR10_1$ and $NR10_2$ clones in the presence (+) or absence (−) of nitrate on days 1 and 7 after addition of nitrate. These figures indicate that the transfected clones produced significantly more nitrite per cell in the presence of nitrate (+) than in its absence (−) and certainly more than the nontransfected controls. Nontransfected controls showed no significant increase in nitrite production when fed exogenous nitrate. These data support the existence of a hybrid or composite redox system in macrophages consisting of the phagocyte iNOS or to a lesser extent eNOS and the truncated barley NR, since increased iNOS activity (due to INF/LPS stimulation) led to increased nitrite production in the presence of nitrate.

Present spectrophotometric evidence indicates that transfection with the NR fragment alters macrophage nitrogen oxide metabolism. Neither serial passage over several months nor freezing has caused any loss of the enhanced $NO_2^-$ production shown by transfectants, thus suggesting stable alteration of metabolism. The production of substantial levels of $NO_2^-$ by nontransfected control cells in media with or without $KNO_3$, can be at least partially accounted for by the catabolism of L-arginine. This activity is known and has been attributed to a constitutive NOS. The facts that culture media repeatedly showed no detectable LPS by the Limulus amebocyte assay and that nitrite production of nontransfected macrophages is almost completely inhibited by $N^g$MMA and L-can. indicate that a constitutive NOS (cNOS) is functioning.

Poliferation kinetics suggest that transfected macrophages produced higher levels of nitrite on a per cell basis whether in the presence or absence of added nitrate. Nitric oxide and nitrite are known to inhibit mitochondrial respiration leading to stasis or death. From the lack of proliferation exhibited, it appears that transfected cells cultured in the presence of added nitrate produced the greatest amounts of nitrite. While it is true that nontransfected cells actually produced greater concentrations of nitrite in the latter stages of culture, the greater cell numbers exhibited by nontransfectants led to a lower per cell production of nitrite. Despite high nitrite levels, macrophage survival was remarkably good until day 7.

The cell lines of the present invention may be employed for the biological, immunological and neurological studies of NO metabolism. The cells can be injected into tumors, infected areas or tissue to be activated. The cells can then be activated with oral nitrate after an appropriate time for seeding into the target tissue. These cell lines can also be used for the production of diazomelanin (DM) and diazoluminomelanin (DALM) as disclosed in U.S. patent application Ser. No. 779,694, filed Oct. 21, 1991. Briefly, production of DM is achieved by culturing the cells in a medium containing a nitrate source and 3-amino-L-tyrosine under suitable metabolic conditions. Production of DALM is achieved by culturing the cells in a medium containing a nitrate source, luminol and 3-amino-L-tyrosine under suitable metabolic conditions.

Various modifications may be made to the invention as described without departing from the spirit of the invention or the scope of the appended claims.

We claim:

1. A mammalian cell line formed by transfecting the murine macrophage RAW 264.7 with a barley nitrate reductase 1.1 kilobase pair gene fragment.

* * * * *